United States Patent [19]
Vorlop et al.

[11] Patent Number: 5,310,786
[45] Date of Patent: May 10, 1994

[54] REVERSIBLY PRECIPITABLE, WATER-SOLUBLE POLYMER CONJUGATES

[75] Inventors: Klaus-Dieter Vorlop; Kerstin Steinke, both of Braunschweig; Dieter Wullbrandt, Hofheim am Taunus; Merten Schlingmann, Königstein am Taunus, all of Fed. Rep. of Germany

[73] Assignee: Hoechst Aktiengesellschaft, Frankfurt am Main, Fed. Rep. of Germany

[21] Appl. No.: 106,696

[22] Filed: Aug. 16, 1993

Related U.S. Application Data

[63] Continuation of Ser. No. 683,495, Apr. 10, 1991, abandoned, which is a continuation of Ser. No. 529,723, May 29, 1990, abandoned, which is a continuation of Ser. No. 141,126, Jan. 6, 1988, abandoned.

[30] Foreign Application Priority Data

Jan. 8, 1987 [DE] Fed. Rep. of Germany ....... 3700308

[51] Int. Cl.$^5$ ................................................ C08F 8/42
[52] U.S. Cl. .................... 525/54.1; 435/179; 435/180; 435/188; 525/54.11; 525/54.2; 525/54.21; 525/54.23; 525/327.3; 525/328.2; 525/328.4; 525/328.8; 525/329.4; 525/366; 525/367; 525/368; 525/369; 525/370; 525/371; 525/372; 530/387.1; 530/387.9; 530/388.2; 530/388.26; 530/388.85; 530/403; 530/412; 530/413; 530/421
[58] Field of Search ............ 525/54.1, 54.11, 54.2, 525/54.21, 54.23, 327.3, 328.2, 328.4, 328.8, 329.4; 530/387.1, 387.9, 388.2, 388.26, 388.85, 403, 412, 413, 421; 435/179, 180, 188

[56] References Cited

U.S. PATENT DOCUMENTS

| | | |
|---|---|---|
| 4,067,876 | 1/1978 | Ferruti et al. . |
| 4,070,348 | 1/1978 | Kraemer et al. . |
| 4,166,902 | 9/1979 | Ferruti et al. . |
| 4,169,923 | 10/1979 | Ferruti et al. . |
| 4,190,713 | 2/1980 | Kraemer et al. . |
| 4,208,309 | 6/1980 | Kraemer et al. . |
| 4,352,884 | 10/1982 | Nakashima et al. ............. 435/7 |
| 4,511,694 | 4/1985 | Krämer et al. ............... 525/54.1 |
| 4,593,073 | 6/1986 | St. Pierre et al. . |

FOREIGN PATENT DOCUMENTS

| | | |
|---|---|---|
| 0058767 | 9/1982 | European Pat. Off. . |
| 2546242 | 4/1976 | Fed. Rep. of Germany . |
| 1431940 | 4/1976 | United Kingdom . |

OTHER PUBLICATIONS

Patent Abstracts of Japan, vol. 10, No. 17, (C-324)(2074) (1986).
Mosbach, Methods in Enzymology, vol. XLIV, pp. 53-107 (1976).
Chibata, Immobilized Enzymes, pp. 9-71 (1978).
Feder, "Biochemical and Biophysical Research Communications", vol. 32, No. 2, 1968, pp. 326-332.

*Primary Examiner*—Bernard Lipman
*Attorney, Agent, or Firm*—Finnegan, Henderson, Farabow, Garrett & Dunner

[57] ABSTRACT

The invention relates to polymer conjugates which are reversibly precipitable from aqueous solution and are composed of a carrier polymer which is soluble in aqueous medium and of a catalytically active compound which is chemically bonded thereto. The invention also relates to a process for the preparation of polymer conjugates of this type, and to the use thereof in homogeneous catalysis, especially biocatalysis.

11 Claims, 2 Drawing Sheets

REVERSIBLY PRECIPITABLE, WATER-SOLUBLE POLYMER CONJUGATES

This application is a continuation of application Ser. No. 07/683,495, filed Apr. 10, 1991, now abandoned, which is a continuation of application Ser. No. 07/529,723, filed May 29, 1990, abandoned, which is a continuation of application Ser. No. 07/141/126, filed Jan. 6, 1988, abandoned.

The invention relates to polymer conjugates which are reversibly precipitable from aqueous solution and which are composed of a carrier polymer which is soluble in aqueous medium and of a catalytically active compound which is chemically bonded thereto. The invention likewise relates to a process for the preparation of polymer conjugates of this type, and to the use thereof in homogeneous catalysis, in particular biocatalysis.

Carrier-bound catalysts, in particular carrier-bound (immobilized) enzymes have a multiplicity of uses, for example in medical analytical methods, in the manufacture of products in pharmacy (antibiotics) and crop protection, in the manufacture of foodstuffs, and in obtaining optically active substances (racemate resolution for amino acids).

However, economic use of catalysts of this type is only advantageous when the catalyst, which is usually very costly, can be recovered, i.e. used several times. One solution to this is the immobilization of such catalytically active compounds. In this form they can be easily manipulated, while retaining their catalytic properties. The following methods of immobilization have been described:

1. Immobilization of catalytically active compounds on or in solid particles (heterogeneous catalysis) by:
   inclusion in a (polymeric) matrix
   adsorption
   covalent bonding
   microencapsulation
2. Immobilization of catalytically active compounds by covalent bonding to water-soluble polymers (homogeneous catalysis).

The immobilized catalysts are often stabilized compared with the free form.

The use of water-soluble carrier polymers, such as polyethylene glycols, for the immobilization of catalytically active compounds is employed for stabilizing and increasing the molecular weight of enzymes and cofactors in membrane reactors.

The use of heterogeneous catalysts and membrane reactors is unsuitable for reactions of high molecular weight, water-insoluble substrates, or in reactions with insoluble products. The development of a water-soluble polymer which is capable of immobilization and can be recovered by precipitation would make possible both the processing of high molecular weight substances and reactions with water-insoluble products.

A multiplicity of methods for the immobilization of catalytically active compounds, in particular enzymes, is known. A detailed review is given, for example, in Methods in Enzymology, Vol. XLIV, "Immobilized Enzymes", (Academic Press, 1976) and in J. Chibata: Immobilized Enzymes (Kodansha Ltd., John Wiley & Sons, 1978). A way which is often described is the adsorption or ionic or covalent bonding of enzymes to carriers.

Carrier substances described in German Auslegeschrift 2,237,316 are swellable, cross linked bead polymers which are obtained by copolymerization of monomers containing reactive groups, crosslinking monomers and hydrophilic monomers. Reactive groups disclosed in this citation are the halogenoalkyl, the epoxide, the carbonyl chloride, carboxylic anhydride, carbonyl azide, carboxylic phenyl ester and hydroxamic acid groups.

German Offenlegungsschrift 27 22 751 describes the preparation of bead polymers as carrier polymers from acryl/methacrylamide and/or methylene-bis-acryl/methacrylamide. These polymers also contain, where appropriate, further comonomers which can undergo radical polymerization and have an oxirane, carboxylic anhydride, carbonyl chloride carbonyl azide, carboxylic phenyl ester or hydroxamic acid group.

However, all these carrier polymers known from the literature have the disadvantage that they are insoluble in water. Although enzymes or other catalytically active substances can be chemically bonded to these polymers, their activity is far less than fully utilized because the active surface is still relatively small compared with a dissolved polymer having chemically bonded catalytically active compounds.

Water-soluble polymer conjugates which flocculate on raising the temperature and/or adding salt, and thus can be removed from a reaction solution by straightforward physical methods of separation, have now been found. Moreover, the precipitation point of these polymer conjugates can be adjusted within a wide temperature range (about 10° to 80° C.) and suited to the particular working temperature of the chemically bonded, catalytically active component. The precipitation point is adjusted by varying the monomer composition. The flocculation temperature is advantageously chosen such that it is only slightly above the most favorable working temperature of the bonded, catalytically active component.

Hence the invention relates to: a water-soluble polymer conjugate composed of a carrier polymer and of a catalytically active compound chemically bonded thereto, which comprises the polymer conjugate being composed of a water-soluble carrier polymer which is reversibly precipitable from aqueous solution by raising the temperature—preferably in the range 10°-80° C.—and/or by addition of salt, and of a catalytically active compound.

In the statements made hereinbefore and hereinafter, catalytically active compounds are defined as enzymes, coenzymes, antigens, antibodies, metals or metal complexes (chiral agents), amino acids and affinity materials, especially enzymes.

The preferred water-soluble and reversibly precipitable polymer conjugates are those in which the carrier polymer is soluble in water and contains repeating monomer units which are hydrophilic and/or hydrophobic.

The particularly preferred water-soluble and reversibly precipitable polymer conjugates are those in which the carrier polymer is soluble in water and, apart from the repeating hydrophilic and/or hydrophobic monomer units, also contains repeating monomer units which have a reactive side chain to which the catalytically active compound is chemically bonded.

Very particularly preferred water-soluble and reversibly precipitable polymer conjugates are those in which the water-soluble carrier polymer is composed of repeating monomer units of the formula I (I)

in which $R^1$ and $R^3$ are identical or different and denote hydrogen or straight-chain or branched $C_1$-$C_3$-alkyl, and $R^2$ denotes straight-chain or branched $C_1$-$C_3$-alkyl, and of at least one other repeating monomer unit selected from the compounds of the formula II, III and IV (II)

(III)

(IV)

$R^1$ being defined as indicated for formula I, $R^4$ being a hydrophobic group and denoting straight-chain $C_1$-$C_6$-alkyl which, in the case of $C_3$-$C_6$-alkyl radicals, can also be branched or cyclic, $R^5$ being an activated group and being 3,4-epoxycyclohexyl or a substituent of the formula V (V)

A being oxygen, sulfur or an NH group, and $R^6$ being a $-(CH_2)_n-Z$ radical, in which n denotes a number from 1 to 6, and Z denotes amino, hydroxyl, carboxyl, carbonyl, or 1,2-epoxyethyl, X being an hydrophilic group and denoting an OH, $NH_2$ or SH group, and Y denoting oxygen or sulfur.

The invention furthermore relates to a process for the preparation of the polymer conjugates according to the invention, which comprises reaction of a water-soluble carrier polymer which is reversibly precipitable from aqueous solution, by raising the temperature and/or addition of salt, with a catalytically active compound, where appropriate after previous chemical modification of the side chains present on the carrier polymer.

Finally, the invention relates to the use of the polymer conjugates according to the invention in homogeneous catalysis, especially in homogeneous biocatalysis.

The invention is described in detail hereinafter.

The carrier polymer must meet the following requirements:

a) completely soluble in water at 1°-20° C., b) precipitable by raising the temperature, preferably in the temperature range 10°-80° C., and/or by addition of salt, c) can be completely redissolved when the temperature or the salt concentration is lowered (reversibly precipitable), d) can be completely and straightforwardly removed even in the presence of other soluble polymers or solids.

Examples of carrier polymers which meet these requirements from the outset are poly-N-alkylacrylamides, poly-N-alkylalkylacrylamides or copolymers of the corresponding monomer units or alkyl-celluloses, in which the said alkyl radicals have 1-4 carbon atoms and are branched or unbranched and saturated. Carrier polymers of these types are described—although used for another purpose—for example in Japanese Patent 60-170-607, Japanese Patent 60-170-608, Japanese Patent 60-170-609 or Handbook of water soluble gums and resins, R. L. Davidson, McGraw-Hill Book Company 1980.

However, it is also possible in general, by copolymerization with suitable comonomers, for water-soluble polymers which are prepared by polymerization of monomers and which either are not reversibly precipitable at all or have a precipitation point above 80° C., such as, for example, polyvinyl ethers, polyvinyl acetates or polyvinyl alcohols (other water-soluble polymers are indicated, for example, in Encyclopedia of Polymer Science and Technology, Interscience Publishers New York, Vol. 12, pages 618-626, 1971) to be made "precipitable" to an extent such that they are reversibly precipitable in the temperature range of about 10°-80° C. and meet the abovementioned requirements.

Thus, in general, the precipitation point of every water-soluble, reversibly precipitable polymer which can be prepared by polymerization can be adjusted within wide limits by copolymerization with suitable comonomers.

Suitable comonomers are those having hydrophilic or hydrophobic side chains. Incorporation of hydrophilic comonomers shifts the precipitation point to higher temperatures, and that of hydrophobic comonomers shifts it to lower temperatures. Suitable comonomers of this type are monomers which can undergo radical polymerization and have in a side chain at least one of the following substituents, such as hydrophilic substituents: OH, $NH_2$ or SH, hydrophobic substituents: alkyl, alkyloxy, alkylthio or alkylamino or alkyloxy-carbonylalkyl or alkylcarbonyloxyalkyl or phenyl, or alkyl-, alkyloxy-, alkylthio- or alkylamino-substituted phenyl, the abovementioned alkyl radicals having 1-18 carbon atoms, and it being possible for the alkyl radicals to be branched, unbranched or cyclic, and the alkyl radicals being preferably saturated.

Where appropriate, it is possible for these substituents to be bonded via spacer groups to the polymerizable part of the monomer unit. The spacer group is preferably composed of a branched or unbranched, saturated $C_1$-$C_8$-alkylene, -alkyleneoxy, -alkylenecarbonyl or -alkylenethiocarbonyl radical.

In order to facilitate bonding of the catalytically active compound to the carrier polymer, the polymer also contains, where appropriate, further monomer units substituted with reactive groups (functionalized carrier polymer). Examples of such reactive groups which may be mentioned here are:

ethyl- or cyclohexyloriranes, $NH_2$, OH, COOH or CHO groups. The reactive substituents can also, where appropriate, be bonded via the spacer group which is described above to the part of the monomer which can undergo radical polymerization.

The preferred carrier polymers are those composed of repeating monomer units of the formula I and of at least another repeating monomer unit selected from the compounds of the formula II, III and IV.

Particularly preferred polymers are those in which
$R^1$ denotes hydrogen, methyl or ethyl,
$R^2$ denotes ethyl, n- or i-propyl,
$R^3$ denotes hydrogen, methyl or ethyl,
$R^4$ denotes straight-chain or branched $C_1$-$C_4$-alkyl,
$R^5$ denotes 3,4-epoxycyclohexyl or a substituent of the formula V,
$R^6$ denoting a —$(CH_2)_n$—Z radical with n=1 to 3, and Z denoting carbonyl or 1,2-epoxyethyl, and A being oxygen or an NH group,
X denotes an OH or $NH_2$ group, and
Y denotes oxygen.

The carrier polymer is very particularly preferably composed of: N-isopropylacrylamide or N-isopropylmethacrylamide (of the formula I) and a compound selected from methacrylamide, methyl acrylate and glycidyl methacrylate or glycidyl acrylate (of the formulae II, III and IV).

The carrier polymer expediently contains only one of the hydrophilic or hydrophobic comonomer components. However, it is also perfectly possible to use mixtures of these components.

The carrier polymers which are preferably used contain 0.2–80% by weight, based on the weight contributed by the polymer of the formula I, of the comonomer components selected from the compounds of the formula II, III and IV, combinations of all three substances also being permissible. Their content of these comonomers is preferably 0.2–40% by weight, particularly preferably 5–40% by weight. If combinations of the compounds of the formula II, III and IV are used, then the indicated figures relate to their total weight.

Where comonomer components of the formula IV are present alone or mixed with others in the carrier polymer, their weight as a proportion of the weight of the remaining polymer is preferably 0.2–15%. A proportion by weight of 0.2–3% is particularly preferred.

Figure 1:
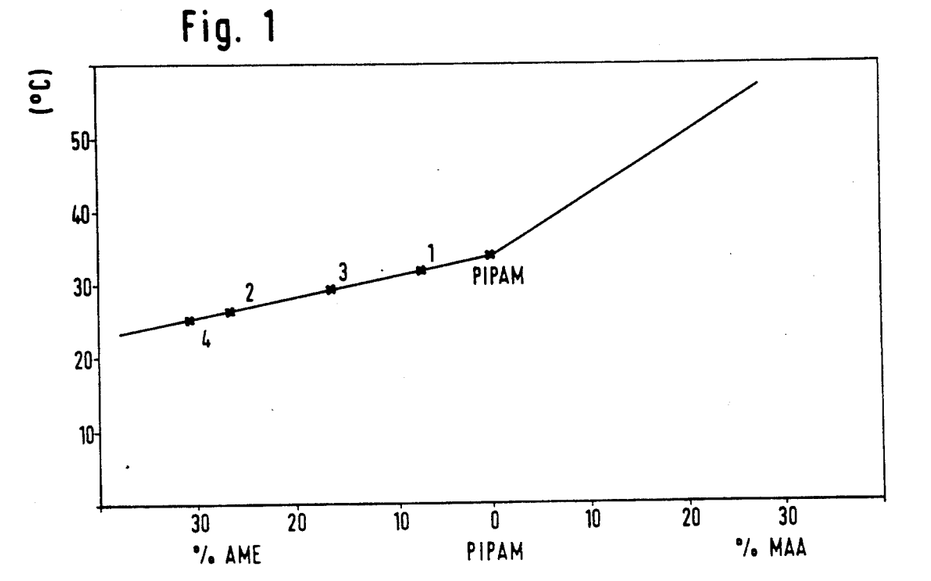

There is a linear relation between the precipitation temperature and the content of hydrophilic or hydrophobic comonomer. This relation is clearly evident from FIG. 1, which shows the percentage content (based on the finished polymer) in the copolymer, and this depicts, by way of example, that for poly-N-i-propylacrylamide (PIPAM) with varying proportions of methyl acrylate (AME) and methacrylamide (MAA).

It is possible in this way to prepare carrier polymers with a defined precipitation temperature depending on their use.

Those monomers which are required for the polymerization and cannot be bought can be prepared in a straightforward manner. For example, the N-alkyl-substituted acryl/methacrylamides (of the formula I or II) are obtained by reaction of acryloyl/methacryloyl halide, preferably acryloyl/methacryloyl chloride, with the desired alkyl- or di-alkylamines.

The monomeric acrylates of the formula III and IV are prepared, for example, by reaction of acryloyl/methacryloyl halides, preferably chlorides, with the appropriate alcohols or mercaptans.

The monomers of the formula V can be prepared, for example, by reaction of acryloyl/methacryloyl halides, preferably chlorides, with alcohols, mercaptans or primary amines, the substituent Z being protected, where appropriate, before this reaction with a suitable protective group, for example ester, acetal, ether or tosylate.

The corresponding higher alkylacrylamides are obtained, for example, from the 2-ethyl- or 2-propylacroleins by oxidation with, for example, chromic acid to give the corresponding acrylic acids (see Organikum, Organisch Chemisches Grundpraktikum (Basic Course in Practical Organic Chemistry) 15th revised edition, page 447, VEB Deutscher Verlag der Wissenschaften, Berlin 1976), which are subsequently converted into the carbonyl halides which then react, as described above, with alcohols or amines to give the desired alkylacrylamides/acrylic acids.

The carrier polymers are obtained—when they cannot be used directly like the alkylcelluloses—by radical polymerization of the monomer units in a solvent, preferably water.

The polymerization is initiated in a manner known per se, for example by UV light or high-energy radiation, but as a rule by a radical-forming initiator which is soluble in the monomer mixture. Examples of suitable initiators are soluble peroxodisulfates, benzoyl peroxide, tert.-butyl hydroperoxide, cumene peroxide, methyl ethyl ketone peroxide, lauroyl peroxide, tert.-butyl perbenzoate, tert.-butyl diperphthalate, azodiisobutyronitrile, 2,2'-azobis(2,4-dimethylvaleronitrile), 2-phenylazo-2,4-dimethyl-4-methoxyvaleronitrile, 2-cyano-2-propylazoformamide, azodiisobutylamide, or dimethyl, diethyl or dibutyl azobis-methylvalerate. It is preferable to use an ammonium peroxodisulfate/sodium thiosulfite mixture. Based on the amount of monomer, about 0.01 to 2% by weight, preferably 0.1 to 1% by weight, of initiator is used.

The reaction is expediently carried out with exclusion of oxygen in an inert gas atmosphere, such as nitrogen or argon. The reaction times amount to 10 minutes to 10 hours, preferably 30 minutes to 5 hours. The polymerization can be stopped, for example by blowing in air or oxygen, at any desired time. The reaction is preferably stopped when there is no longer any detectable increase in viscosity. The reaction temperature is between 0° and 40° C., preferably between 0° and 20° C.

To prepare the carrier polymers which are preferably used there are added—based on the amount of monomer substance of the formula I which has been previously introduced—0.2–80% by weight, preferably 0.2–60% by weight, of at least one monomer selected from the compounds of the formula II, III and IV. The amount of comonomer which is added can also be composed of any desired mixture of the monomers of the formula II, III and IV; however, it is more advantageous, for the adjustment of the precipitation temperature to be as accurate as possible, to use only one comonomer component of formula II or III.

If the carrier polymer is to contain monomer units of the formula IV, this monomer is added in an amount of 0.2–20% by weight, preferably 0.2–10% by weight, based on the amount of the remaining monomers which have previously been introduced.

The total concentration of all the monomers in the solvent is 1-30% by weight, preferably 5-15% by weight.

The final percentage composition of the polymer can be determined only by quantitative elemental analysis. It is difficult to establish an accurate correlation between the monomers used and the content of these monomer units in the polymer, because the final composition depends on many parameters, such as the reaction temperature, time and yield. For this reason, the percentages of the monomer units in the carrier polymer, and not the composition of the monomers before the reaction, are plotted in FIG. 1.

The carrier polymers which are described above are now reacted, in a manner known per se, with catalytically active substances to give the polymer conjugates according to the invention. Catalytically active compounds are defined as those substances which are able to bring about a chemical change in a reactant which is brought into contact with them without themselves undergoing a permanent structural or chemical change during this. Thus, they themselves emerge unchanged from the reaction. Examples of such catalytically active components which may be mentioned are:

a) Metals or metal complexes (chiral agents) for example for enantioselective hydrogenation, polymerization or hydroformylation, hydrosilylation (homogeneous transition and noble metal catalysis), examples which may be mentioned here are:

phosphine complexes such as [RhCl(PPh$_3$)$_3$]Patent 92 031
    [Co$_2$(CO)$_8$] cf. U.S. Pat. No.
    [Na$_2$PdCl$_4$] cf. German Patent 2 330
    [Rh$_2$Cl$_2$(C$_2$H$_4$)$_4$] 133 199
    Ph=phenyl for the preparation of pure optical antipodes, especially amino acids, examples which may be mentioned here are:

phosphate complexes of: [Rh$_2$Cl$_2$(C$_2$H$_4$)$_4$] German Patent 27 18 533
    [Rh$_2$Cl$_2$(Cod)$_2$] German Patent
    [Rh(Norban)$_2$]ClO$_4$ Japanese Patent 59 090
    Cod=cyclooctadiene, norban=norbornadiene.

In the said metal complexes, the transition metals in turn usually coordinated to organic radicals having terminal-PPh$_2$ groups. These organic radicals can be bonded in the same way to the active side chain of the carrier polymers described above, this bonding being described in a large number of the abovementioned citations for resins or other water-insoluble carrier polymers.

b) Affinity materials for example for the isolation of, where appropriate, high molecular weight enzymes affinity materials are defined as substrates or substrate analogs which can be covalently bonded to a polymeric carrier and which couple, with their "free" side, to a type-specific enzyme which, after removal of the carrier polymer/substrate/enzyme conjugate from the reaction medium, can be easily eliminated again from the substrate and, in this way, isolated. This is described, for example, in: U.S. Pat. No. 3,941,657 (D-amino-acid oxidase) Immobilized Enzymes, Preparation and Engineering, Recent Advances 1979, J. C. Johnson Solid Phase Biochemistry, Analytic and Synthetic Aspects, W. H. Souten, Volume 66 c) Amino acids for example for protein synthesis (analogous to the Merrifield resin), see, for example, Solid Phase Biochemistry, Analytic & Synthetic Aspects, W. H. Scouten, Vol. 66 d) Antibodies e) Antigens f) Enzymes for example from the hydrolase group, such as:

Proteases: α-chymotrypsin, trypsin, thermolysin, pepsin
    Acylases:
        lipases, for example from *Candida cylindracea* or from porcine pancreas
    Esterases: porcine liver esterase, cholinesterases
    Amidases: penicillin acylase g) Coenzymes for example adenosine triphosphate (ATP) or dinucleotide (NAD/NADH) U.S. Pat. No. 3,957,748

Enzymes and coenzymes are particularly suitable. Of the enzymes, the immobilization of proteases and acylases is particularly satisfactory.

One possibility for permanently coupling catalytically active compounds to a carrier is covalent bonding. For this purpose, the reactive groups on the carrier polymer and on the catalytically active component must react together, for example via an amino or hydroxyl group. This takes place a) by direct reaction of the dissolved carrier polymer with the catalytically active compound or b) in the case where the reaction conditions are unsuitable for the catalytically active compound—after previous chemical modification of the reactive side chain of the carrier polymer or c) with simultaneous addition of a "reaction promoter".

One example of the direct reaction of the carrier polymer with a catalytically active component is depicted in reaction scheme a) below Examples of epoxide-containing carrier polymers which can be used are the polymers which have an oxirane-containing side chain, for example 1,2-epoxyethanes or 3,4-epoxycyclohexanes.

For those catalytically active compounds which cannot be coupled under reaction conditions a) it is advantageous to change (to modify chemically) the reactive side chain of the carrier polymer before the reaction in such a way that the reaction can take place under milder conditions (reaction scheme b)). For example the epoxide group can first be cleaved hydrolytically to form a diol, which is then reacted, for example with a cyanogen halide, in particular cyanogen bromide, to give an imidocarbonic di-ester, which can then be reacted under mild conditions with the appropriate catalytically active compound (see reaction scheme b)).

-continued

Once again, it is possible in this case to start from epoxide-containing carrier polymers.

Polymers having a carboxyl-containing side chain can be reacted, for example in the presence of dialkylcarbodiimides, especially dicyclohexylcarbodiimides (DCC), with the catalytically active component (reaction scheme c)). In this case, DCC acts as a "reaction promoter", that is to say facilitates the reaction of the carboxylic acid with the amino or hydroxyl group of the catalytically active component. The reaction takes place as shown in the scheme below:

▨ = carrier polymer, Ⓚ = catalytically active compound

R = $C_1$–$C_8$-alkyl/cycloalkyl.

Carrier polymers having amino, hydroxyl or carbonyl groups in the reactive side chains can be loaded with the catalytically active component either directly in accordance with reaction scheme a) or in accordance with one of the variants b) or c).

The best procedure for coupling the catalytically active compounds to the functionalized carrier polymer is such that the carrier polymer is first dissolved in an aqueous solvent, preferably water, and then the appropriate catalytically active compound is added, either as the pure substance or likewise in an aqueous medium, preferably dissolved in water. The pH of the solution should preferably be maintained during this in the region in which the appropriate catalytically active substance and the carrier polymer are stable. This is expediently carried out using suitable buffers. The preferred ranges for the various process variants a), b) and c) are indicated in the relevant schemes. The reaction time is between 0.1 and 70 hours, preferably 10 to 60 hours, in particular 20 to 55 hours. The reaction temperature should be between 1° and 35° C., preferably 3° and 30° C., in particular 5° and 25° C.

The molar ratios of the carrier polymer which is used and is, where appropriate, functionalized, and the catalytically active compound should expediently be chosen such that at least one mole of catalytically active compound is present per mole of activated side chain so that, when conversion is complete, all the available reactive side chains are substituted by the catalytically active compound. However, in order for the conversion to be as complete as possible, it is advantageous to use an excess of catalytically active substance. It may, however, depending on the intended use, also be entirely appropriate for not all the reactive side chains which are present to be reacted with the catalytically active compounds, i.e. less than the stoichiometric amount of the catalytically active compounds is used.

Finally, the polymer conjugate according to the invention is precipitated, removed from the solution and, where appropriate, purified by reprecipitation once or several times. Precipitation is effected by raising the temperature and/or addition of salt.

The solubility in water of the polymer conjugates according to the invention is determined by two structural elements, the hydrophilic and the hydrophobic side chain of the carrier polymer.

The thermal precipitation of the polymer conjugates according to the invention is completely reversible. Both the dissolved and the precipitated form of the polymer is, once reached, relatively stable.

There are thus two possibilities for the precipitation of the polymer conjugate. Either the temperature is raised at a given salt concentration, or salt is added to the solution at a given temperature (for example room temperature). In both cases phase separation occurs when, owing to the influence of the temperature or the salts, the solvating envelope is so greatly destabilized that the influence of the hydrophobic groups dominates.

The solubility in water of the polymer conjugate decreases in the presence of salt, for example NaCl. It emerges that there is a linear relation between the salt concentration and the solubility of the polymer conjugate.

At every temperature which is below the critical temperature for dissolution of the polymer conjugate in pure water it is possible for the solvating envelope of the macromolecules to be broken down, i.e. destabilized, by addition of a critical salt concentration, to such an extent that phase separation occurs.

Every salt and every ion has a characteristic flocculating power. Highly solvated ions have a strong dehydrating effect, and even a small concentration of them brings about detachment of the macromolecular solvating envelope. To obtain the same effect with poorly solvated ions it is necessary to add them in a larger amount. Precipitation tests with $Na^+$ and $NH_4^+$ ions confirm this. The flocculating power of other ions can be estimated from the Lyotropic series of F. Hofmeister (R. Brdička, Grundlagen der physikalischen Chemie, (Basic Physical Chemistry), 15th edition, VEB Deutscher Verlag der Wissenschaften, Berlin 1982, pages 668-672):

Sequence of decreasing precipitating power

Anions: $CO_3^{2-}$, $SO_4^{2-}$, $PO_4^{3-}$, acetate$^-$, $Cl^-$, $Br^-$, $I^-$ Cations: $Mg^{2+}$, $Ca^{2+}$, $Na^+$, $K^+$, $NH_4^+$ All the possible combinations of cations and anions from the above table are suitable according to the invention, for example calcium chloride, sodium sulfate, sodium acetate, sodium chloride, sodium bromide, sodium iodide, potassium chloride, potassium bromide, potassium iodide, potassium sulfate, in particular sodium chloride.

The flocculation of the polymer conjugate according to the invention is also completely reversible in the presence of salts. If the parameters of temperature and/or salt concentration are changed so that the hydrophilic effect predominates, the polymer conjugate dissolves again completely.

Figure 2:
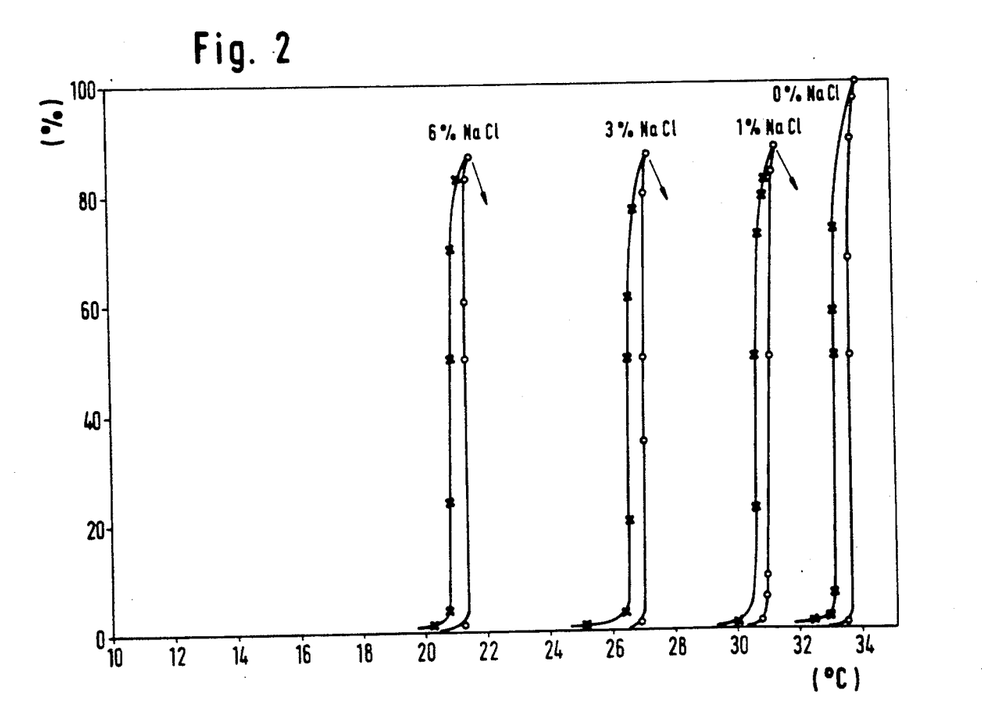

FIG. 2 shows the dependence of the turbidity on the temperature, depicted for a 0.1% strength solution of the polymer conjugate from Example 7. The turbidity was determined by photometry. 100% turbidity corresponds to complete precipitation of the polymer conjugate, It is possible to add to the solution, for the precipitation of the polymer conjugate according to the invention, 2-90% by weight, preferably 5-70% by weight—based on the mass of the dissolved polymer conjugate—of salt, preferably as solid, but also in dissolved form.

Apart from water, suitable solvents for the polymer conjugates according to the invention are aqueous solutions which contain up to 20% by weight of an organic solvent which is completely and infinitely miscible with water, such as methanol, ethanol or acetone.

The main advantage of the polymer conjugates according to the invention is that they are soluble in water and they are precipitable reversibly and controllably. Even after having been "used" several times, that is to say after dissolving and reprecipitating several times, there is an only inconsiderable decrease in the activity of the catalytically active substances bonded to these carrier polymers (see Example 9).

It is possible, using the polymer conjugates according to the invention, to carry out catalytic reactions of immobilized
- enzymes
- coenzymes
- antibodies
- antigens
- affinity materials
- amino acids
- metals or metal complexes (chiral agents)

in homogeneous phase, it being possible to recover, and use several times, the catalytically active material which is used. This avoids the disadvantages of heterogeneous catalysis, such as:
- poor utilization of the catalyst which is present
- inhibition of diffusion (high molecular weight particles, in particular, reach the catalyst only poorly)
- possible inactivation of the catalyst owing to a pH gradient
- limitation of the size of the precursor and product by the pore size of the carrier material
- diminution in activity due to blockage of pores and it is possible to use fully the advantages of homogeneous catalysis, such as:
- high reaction rate
- breakdown and modification of high molecular weight substrates
- preparation of high molecular weight products
- reaction with insoluble products without the necessity to have recourse to the elaborate separation which was hitherto customary for this.

The invention is illustrated in detail hereinafter by means of examples.

EXAMPLE 1

4.2 g of N-isopropylacrylamide (NIPAM) and 0.76 g of methyl acrylate (MA) are dissolved in 50 ml of degassed water. The monomer solution is equilibrated at 15° C., excluding oxygen. The polymerization is started by initially adding 1 ml of 0.5% by weight ammonium peroxodisulfate and 1 ml of 0.5% by weight sodium thiosulfite as aqueous solution to the monomer solution.

The polymerization is stopped after 96 minutes by blowing in air.

General working-up:

The reaction solution is heated, without stirring, until turbidity appears, and crystalline sodium chloride is added, stirring vigorously. The polymer precipitates out, the solid is isolated by decantation, and the polymer is precipitated out twice more from aqueous solution, as described.

Yield 65% (polymer 1)

EXAMPLES 2-4

As in Example 1, copolymers with different monomer contents are synthesized, as shown in Table 1 below.

TABLE 1

| Polymer | Concentration NIPAM | [g] MA | Polymerization temperature °C. | Reaction time (min) | Yield % | Composition of the polymer* % by weight |
|---|---|---|---|---|---|---|
| 1 | 4.2 | 0.76 | 15 | 96 | 65.1 | 92/8,1 |
| 2 | 3.6 | 1.25 | 5 | 65 | 8.9 | 73/27 |
| 3 | 3.25 | 1.32 | 15 | 253 | 85.9 | 83/17 |
| 4 | 3.22 | 1.66 | 15-5 | 240 | 52.1 | 69/31 |

*The polymer composition was determined by proton resonance spectroscopy in deuterochloroform as solvent.

EXAMPLE 5

The procedure is carried out in analogy to Example 1, using N-isopropylacrylamide (4 g) and methacrylamide (0.6 g) as monomers. The polymerization is stopped after 300 minutes by blowing in oxygen.

Yield after purification 52.4% (polymer 5)

EXAMPLES 6-8

Preparation of copolymers having oxirane groups.

The procedure is carried out in analogy to Example 1, under the reaction conditions detailed in Table 2 below:

TABLE 2

| Polymer | NIPAM [g] | GMA [g] | Polymerization temperature [°C.] | Reaction time [min] | Epoxide content % by weight |
|---|---|---|---|---|---|
| 6 | 5.4 | 0.14 | 25 | 40 | 4 |
| 7 | 5.4 | 0.11 | 20 | 240 | 4 |
| 8 | 5.4 | 0.29 | 4 | 40 | 22 |

The polymerization was carried out in 60 ml of water in each case, with 1 ml of ammonium peroxodisulfate (0.5% by weight) and 1 ml of sodium thiosulfite (0.5% by weight) for polymer 6 and polymer 7, and 1 ml of ammonium peroxodisulfate and 0.5 ml of sodium thiosulfite (for polymer 8).

Purification of copolymers 6-8:

1 part of acetone is added to 2 parts of the polymerization solution. 12 parts of diethyl ether are added while stirring vigorously. The polymer precipitates out, and the monomers, which are dissolved in the ether phase, are decanted off. The wet polymer mass is dissolved in a little acetone and precipitated out in diethyl ether. This procedure is repeated several times, and the product is then filtered off with suction and dried in vacuo at room temperature.

Determination of the epoxide content:

The epoxide content of the resulting copolymers was determined by titrimetry. 0.5 g of copolymer is dissolved in 50 ml of distilled water, and the pH is adjusted to 7.0 with 0.01 normal sodium hydroxide solution. Subsequently 15 ml of a 0.13 molar thiosulfate solution are added, and the pH is kept constant at 7 by addition of 0.01 normal hydrochloric acid (autotitration).

EXAMPLE 9

Figure 3:
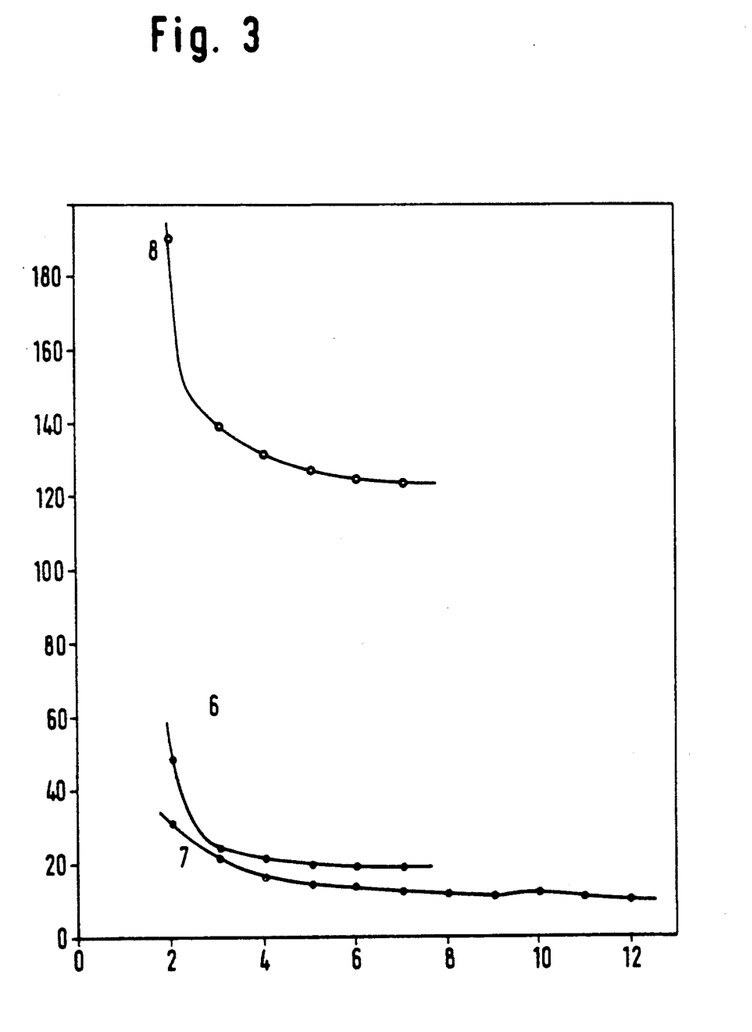

1 g samples of polymers from Examples 6 to 8 are dissolved in 100 ml of 0.05 molar phosphate buffer (pH 7.0) at room temperature. To the solution is added 0.4 g (Example 6), 0.47 g (Example 7) or 0.5 g (Example 8) of trypsin. The mixtures are then stirred at 15° C. for 24 hours. The polymer/enzyme conjugate is purified as described in Example 1. The resulting activities, measured in units per gram of polymer, are shown in FIG. 3 as a function of the precipitations.

The enzyme activity of the conjugate is determined, comparing with free trypsin, by the hydrolytic cleavage of N-benzoyl-L-arginine ethyl ester in 0.05 molar tris buffer (pH 7.5/with addition of 5 mmol of calcium chloride. One unit is defined as: $10^{-6}$ mole/min hydrolyzed N-benzoyl-L-arginine ethyl ester hydrochloride.

EXAMPLE 10

1 g of polymer 8 from Example 8 is dissolved in 100 ml of 2-[4-(2-hydroxyethyl)-1-piperazinyl]ethanesulfonic acid buffer (HEPES buffer) at room temperature (pH 7.3). 0.8 g of thermolysin is added to this solution, which is then stirred at 4° C. for 48 hours. It is subsequently warmed to 30° and the polymer/enzyme conjugate is precipitated out by addition of sodium chloride. This procedure is repeated enough times (about 5 times) for the UV absorption of the washing solution at 280 nm to remain constant.

Yield: 1.15 g; contains 30% by weight thermolysin

The hydrolytic cleavage of 3-(2-furylacryloyl)glycyl-L-leucinamide (FAGLA) is used to determine the activity.

This method is described by J. Feder in Biochemical and Biophysical Research Communications, Vol. 32, (1968), pages 326–332.

Procedure:

3–10 mg of polymer are added to 1.5 ml of substrate solution ($2.45 \times 10^{-3}$ molar) in 0.001 molar phosphate buffer (pH 7.2). After stirring at room temperature for 10 minutes, 50 ml of 1N hydrochloric acid are added. The cleavage activity is determined by HPLC on a reverse phase column.

EXAMPLE 11

0.5 g of polymer from Example 8 is dissolved in 50 ml of 0.05 molar phosphate buffer (pH 7.0). 0.4 g of lipase from Candida cylindracea is added to this solution, and is immobilized at 5° C. The polymer/enzyme conjugate is worked up as in Example 1.

EXAMPLE 12

0.208 g of polymer from Example 8 is dissolved in 40 ml of water which contains 5 mM calcium chloride. About 16 mg of cyclodextrin glycosyltransferase (EC 2.3.1.19) from Bacillus macerans are added to this solution, which is then incubated at 15° C. for 18 hours and at 5° C. for 50 hours.

Unbound enzyme is removed from the polymer/enzyme conjugate by precipitating it out 7 times as in Example 1.

The activity of the cyclodextrin glycosyltransferase was determined as follows: cleavage is carried out with 0.1 g of polymer/enzyme conjugate in 5 mM phosphate buffer pH 7.0 and 5% strength starch solution (potato starch ®Paselli) at 25° C.

The $\alpha$-, $\beta$- and $\gamma$-cyclodextrins formed were determined using HPLC with acetonitrile/water (68:32). The immobilisate shows the same product distribution of $\alpha$-, $\beta$- and $\gamma$-cyclodextrin as the soluble enzyme. The activity for the enzyme/polymer conjugate obtained in this way was 450 units/g of polymer.

We claim:

1. A water-soluble polymer conjugate, comprising:
(a) a water-soluble carrier polymer which is completely soluble in water at a temperature in the range of from about 1° C. to 20° C., which is reversibly precipitable from an aqueous solution by raising the temperature and/or by the addition of a salt, and which is completely redissolvable in the aqueous solution by lowering the temperature or salt concentration and wherein the carrier polymer comprises at least one repeating monomer unit selected from the compounds of the formula I:

$$H_2C=C\begin{smallmatrix}R^1\\\\C=O\\|\\N\\\diagup\phantom{N}\diagdown\\R^2\phantom{NNN}R^3\end{smallmatrix} \qquad (I)$$

in which $R^1$ and $R^3$ are identical or different and denote hydrogen or straight-chain or branched $C_1$-$C_3$-alkyl, and $R^2$ denotes straight-chain or branched $C_1$-$C_3$-alkyl, and of at least one other repeating monomer unit selected from the compounds of the formula II, III and IV:

$$H_2C=C\begin{smallmatrix}R^1\\\\C=O\\|\\X\end{smallmatrix} \qquad (II)$$

$$H_2C=C\begin{smallmatrix}R^1\\\\C=O\\|\\Y\\\diagdown\\R^4\end{smallmatrix} \qquad (III)$$

$$H_2C=C\begin{smallmatrix}R^1\\\\R^5\end{smallmatrix} \qquad (IV)$$

wherein $R^1$ is as defined under formula I, $R^4$ is a hydrophobic group and is a straight-chain $C_1$-$C_6$-alkyl which, in the case of $C_3$-$C_6$-alkyl radicals, can also be branched or cyclic, $R^5$ is an activated group and is 3,4-epoxycyclohexyl or a substituent of the formula V:

$$\begin{smallmatrix}O\\||\\C\phantom{XX}R^6\\\diagup\phantom{X}\diagdown\diagup\\\phantom{XXX}A\end{smallmatrix} \qquad (V)$$

wherein:

A is oxygen, sulfur or an NH group, $R^6$ is a $-(CH_2)_n-Z$ radical, in which n is a number from 1 to 6, and Z is amino, hydroxyl, carboxyl, carbonyl or 1,2-epoxyethyl, X is a hydrophilic group and is an OH, $NH_2$ or SH group, and Y is oxygen or sulfur; and (b) a catalytically active compound chemically bonded to the water-soluble carrier polymer, wherein the catalytically active compound is an enzyme, coenzyme, antigen, antibody, metal, metal complex, affinity material or an amino acid.

2. A polymer conjugate as claimed in claim 1, wherein the carrier polymer has a precipitation point in the range of from about 10° C. to 80° C.

3. A polymer conjugate as claimed in claim 1, wherein the carrier polymer contains repeating hydrophilic or hydrophobic monomer units.

4. A polymer conjugate as claimed in claim 3, wherein the carrier polymer contains repeating activated monomer units.

5. A conjugate as claimed in claim 1, wherein the carrier polymer is composed of a repeating monomer unit of the formula I and of another repeating monomer unit of the formula IV and of 0 to 2 further repeating monomer units selected from the compounds of the formula II and III.

6. A polymer conjugate as claimed in claim 5, wherein the carrier polymer contains a repeating monomer unit selected from the compounds of the formula II and III.

7. A polymer conjugate as claimed in claim 1, wherein $R^1$ denotes hydrogen, methyl or ethyl, $R^2$ denotes n- or i-propyl, $R^3$ denotes hydrogen, methyl or ethyl, $R^4$ denotes straight-chain or branched $C_1-C_4$-alkyl, $R^5$ denotes 3,4-epoxycyclohexyl or a substituent of the formula VI, $R^6$ denoting a $-(CH_2)_n-Z$ radical with n=1 to 3, and Z denoting carbonyl or 1,2-epoxyethyl, and A being oxygen or an NH group, X denotes an OH or $NH_2$ group, and Y denotes oxygen.

8. A polymer conjugate as claimed in claim 1, wherein the compound of the formula I is N-isopropylacrylamide or N-isopropylmethacrylamide, that of the formula II is methacrylamide, that of the formula III is methyl acrylate, and that of the formula IV is glycidyl methacrylate or glycidyl acrylate.

9. A polymer conjugate as claimed in claim 1, wherein the proportion by weight of at least one of the compounds of the formula II, III and IV is from about 0.2 to 80% based on the weight of the monomer unit of the formula I.

10. A polymer conjugate as claimed in claim 6, wherein the proportion by weight of the monomer unit of the formula IV is from about 0.2 to 15% based on the weight of the monomer units of the formula I and II or III.

11. A polymer conjugate as claimed in claim 5, wherein the catalytically active compound is chemically bonded via the activated group of the monomer unit of the formula IV.

* * * * *

UNITED STATES PATENT AND TRADEMARK OFFICE
CERTIFICATE OF CORRECTION

PATENT NO. : 5,310,786

DATED : May 10, 1994

INVENTOR(S) : Vorlop et al.

It is certified that error appears in the above-identified patent and that said Letters Patent is hereby corrected as shown below:

Claim 4, column 15, line 21, "claim 3" should read --claim 1--.

Signed and Sealed this

Twenty-eight Day of February, 1995

Attest:

BRUCE LEHMAN

*Attesting Officer*        *Commissioner of Patents and Trademarks*